Figure 1:
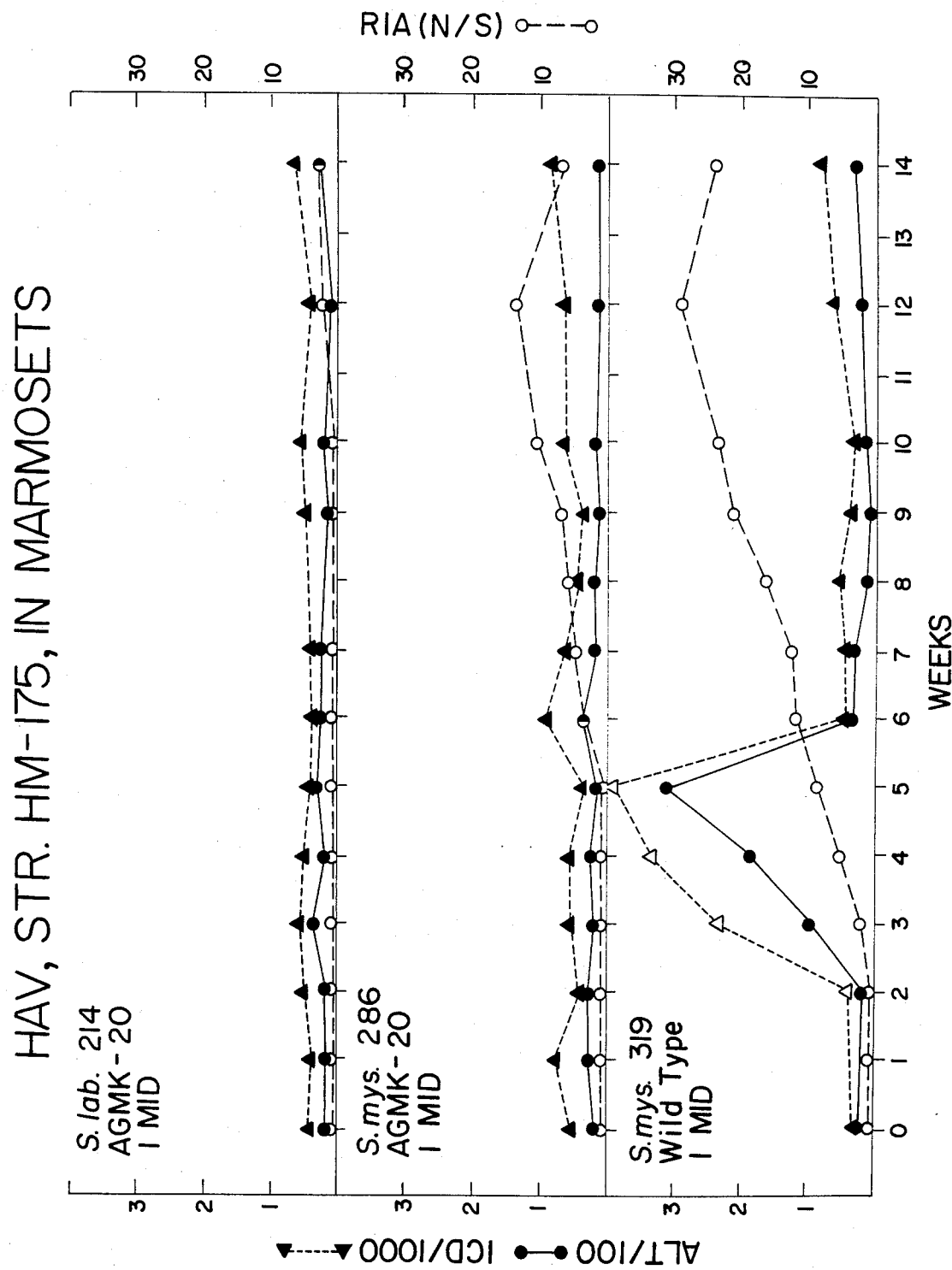

United States Patent [19]

Daemer et al.

[11] Patent Number: 4,620,978
[45] Date of Patent: Nov. 4, 1986

[54] HEPATITIS A VIRUS PURIFIED AND TRIPLY CLONED

[75] Inventors: Richard J. Daemer; Stephen M. Feinstone, both of Washington, D.C.; Ian D. Gust, Fairfield, Australia; Robert H. Purcell, Boyds, Md.

[73] Assignee: The United States of America as represented by the Department of Health and Human Services, Washington, D.C.

[21] Appl. No.: 652,067

[22] Filed: Sep. 19, 1984

Related U.S. Application Data

[63] Continuation-in-part of Ser. No. 366,165, Apr. 7, 1982, Pat. No. 4,532,215.

[51] Int. Cl.[4] .............................................. A61K 39/29
[52] U.S. Cl. ..................................... 424/89; 514/894; 435/237
[58] Field of Search .......................... 424/89; 435/237; 514/894

[56] References Cited

U.S. PATENT DOCUMENTS 4,164,566 8/1979 Provost et al. ...................... 424/89

OTHER PUBLICATIONS

Feinstone, S. M., Daemer, R. J., Gust, I. D., Purcell, R. H., Live Attenuated Vaccine for Hepatitis A, Dev. Biol. Stand. 1983; 54:429-432.

Provost, P. J., Conti, P. A., Giesa, P. A. et al., Studies in Chimpanzees of Live, Attenuated Hepatitis A Vaccine Candidates, Proc. Soc. Exp. Biol. Med. 1983; 172:357-363.

Ticehurst, J. R., Racaniello, V. R., Baroudy, B. M., Baltimore, D., Purcell, R. H., Feinstone, S. M., Molecular Cloning and Characterization of Hepatitis A Virus cDNA, Proc. Natl. Acad. Sci. USA 1983; 80:5885-5889.

von der Helm, K., Winnacker, E. L., Deinhardt, F. et al., Cloning of Hepatitis A Virus Genome, J. Virol. Methods 1981; 3:37-43.

Daemer et al., Infection and Immunity, 32(1):388-393, Apr. 1981.

Purcell et al., "Hepatitis A Virus" (in press).

Primary Examiner—Ronald W. Griffin
Attorney, Agent, or Firm—John S. Roberts, Jr.

[57] ABSTRACT

Human hepatitis A virus (HAV) can be purified by a process in which master seed lots of HM-175 strain of hepatitis A virus are prepared from triply cloned virus by terminal dilution at passage level about 20 or preferably at least 20-30. The clones tested induced minimal or no hepatitis although significant antibody response was provoked in inoculated primates. A method of preparing the triply cloned inoculum is also described.

7 Claims, 2 Drawing Figures

HEPATITIS A VIRUS PURIFIED AND TRIPLY CLONED

This application is a continuation-in-part of pending Ser. No. 366,165 filed April 7, 1982, now U.S. Pat. No. 4,532,215, issued July 30, 1985.

Hepatitis A virus (HAV) has a world-wide distribution. It is responsible for as many as 100,000 cases of hepatitis per year in the United States where, as in most of the developed world, it accounts for perhaps 20-25 percent of clinical hepatitis. It is highly endemic throughout the developing world and infects virtually 100 percent of the population by age ten in such regions. It is a picornavirus with many of the characteristics of an enterovirus and has been classified as such. It is spread principally by fecal-oral contamination and has been responsible for many epidemics of water-borne or food-borne disease. However, it is most commonly spread by person-to-person contact. Parenteral transmission of HAV is very rare.

MATERIAL INFORMATION DISCLOSURE

U.S. Pat. No. 4,164,566 (Provost et al) teaches the development of *in vitro* hepatitis A virus cell cultures. Provost et al, however, use a different strain of HAV which requires at least 5 passages in a sub-human primate in order to produce HAV. The purpose of the parent, Ser. No. 366,165, invention is to show that HAV can be isolated and serially passaged in primary African green monkey kidney (AGMK) cell cultures taken directly from human clinical specimens.

Daemer et al, *Infection and Immunity*, Vol. 32, No. 1, April 1981, pp 388-393.

Purcell et al, "Hepatitis A Virus," in press.

STATEMENT OF DEPOSIT

The HM-175 strain of hepatitis A virus has been deposited in the American Type Culture Collection under the patent procedures prior to the filing of this application, thus affording permanency of the deposit and ready availability to the public upon issuance of a patent.

UTILITY STATEMENT

The triple cloning of master seed lots of the HM-175 strain of hepatitis A virus has resulted in a superior vaccine which produces antibodies but not disease in chimpanzees and other primates such as marmosets. The protection of the chimpanzees challenged by wild-type virus is a significant indicia of vaccine.

THE INVENTION

Cell culture adapted HM-175 human hepatitis A virus at passages 10 and 20 in primary African green monkey kidney cell culture was found to be attenuated for chimpanzees but produced sero-conversions as evidenced by induction of hepatitis A antibody without biochemical evidence of liver disease, Table 1. Chimpanzees which were previously infected with the attenuated strain and produced hepatitis A antibody were protected from developing hepatitis when challenged with infectious hepatitis A virus unless the challenge occurred during the early stage of convalescence when the primary immune response was developing, Table 2. Marmosets inoculated with the same material did develop hepatitis although of lesser severity than with wild type virus (Table 1 and FIG. 1). The stability of attenuation of the tissue culture passaged virus was shown by inoculation (percutaneously, preferably intravenously) of additional chimpanzees with the acute phase stools from previously inoculated animals, Table 3. Recipient animals developed no biochemical evidence of liver disease but hepatitis A antibody was produced.

Figure 2:
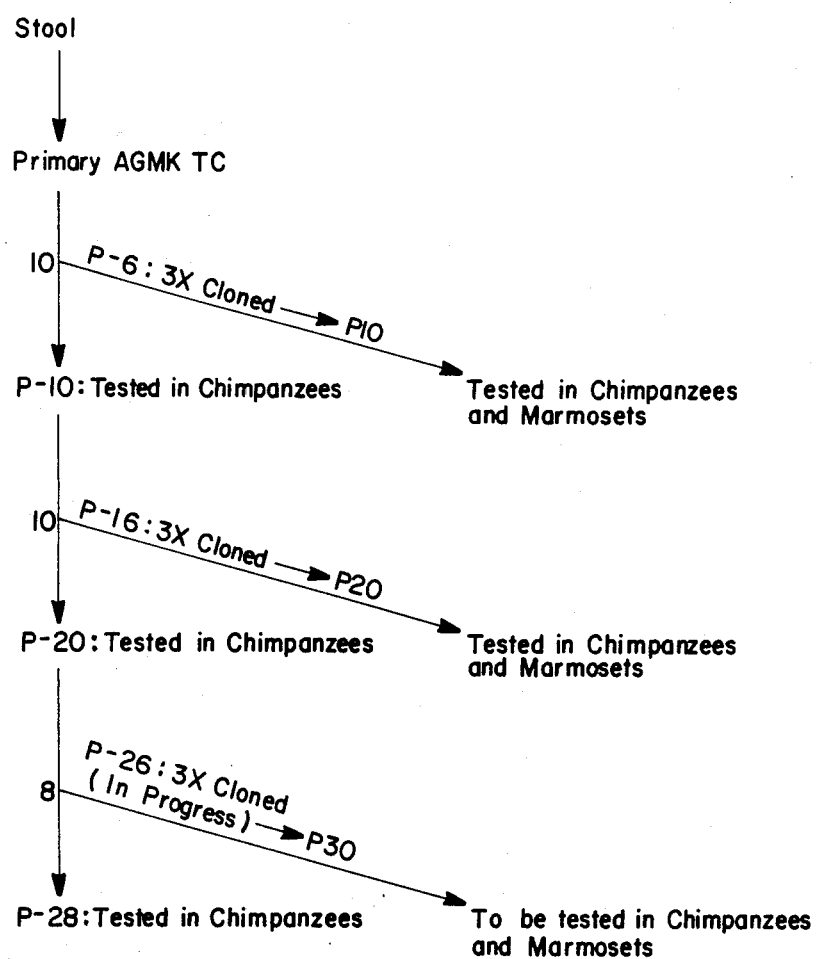

Master seed lots of the HM-175 strain of hepatitis A virus have been triply cloned by terminal dilution at passage levels 10, 20 and 30 (FIG. 2). Two clones from passage level 20 have been evaluated for evidence of attenuation in chimpanzees. Of the two clones tested minimal or no hepatitis was produced in inoculated chimpanzees. With clone #1 antibody was produced in 3 of 6 animals and with clone #2 antibody was produced in 3 of 4 inoculated animals.

The utilization of triply cloned virus material of the HM-175 strain of hepatitis A virus illustrates that it is an effective vaccine for chimpanzees as a live HAV.

This vaccine is utilizable for mammals or higher primates which include man, chimpanzees and marmosets. The triple cloned viral material (3X) is homogeneously superior to the twice cloned (2X) virus for a uniform virus preparation suitable for a vaccine. A master seed lot of virus as explained herein is produced from triply cloned virus by terminal dilutions at passage levels 10 and 20 (Cunningham, *A Laboratory Guide in Virology*, 5th ed., Burgess Pub. Co., 1963, pp 144-145). The purpose of the dilution is that the highest dilution positive tubes of the procedure originated from a single virus particle, thus providing biological uniformity of the product.

In the aspect of the cloning by terminal dilution, the 3X appeared to be optimum in results for a virus or vaccine which is uniform. This selection of 3X agrees with the literature citations as follows: Lennett and Schmidt, "Diagnostic Procedure for Viral and Rickssetial Infections," American Public Health Association, 5 ed., 1979, page 102; and Dulbecco and Vogt, "Plaque Formation and Isolation of Pure Lines With Poliomyelitis Viruses," *J. Exp. Med.*, 99:167-182, 1954.

The HM-175 strain of human hepatitis A virus was imported into this country and is described in *Infection and Immunity*, 32(1), April 1981, pages 388-393.

EXAMPLE 1

Cloning of the virus was done as follows: a pool of uncloned virus was diluted serially $10^{-1}$ to $10^{-8}$. Each dilution was used to inoculate 9 tubes of primary African green monkey cell cultures. The cells were allowed to grow and the virus grew in the cells, harvested after 8 weeks. Each tube was checked for the presence of hepatitis A virus antigen at that time and of the tubes at the highest dilutions, i.e., the $10^{-8}$ dilution, there were some negative, some positive tubes. At this dilution, based upon statistical analysis, the positive tubes originated from a single virus particle. The negative tubes contained no virus. Of the tubes that were positive, two tubes were harvested from each terminal dilution series. They, in turn, were run through the same process of cloning a second and third time. At the third cloning the tubes at the terminal dilution, two of these tubes plus a control uninoculated, were harvested. These positive tubes which originated from a single virus particle were expanded to produce a master seed lot. The master seed lots were then grown up and used for chimpanzee experiments (FIG. 2).

EXAMPLE 2

Use of Master Seed Material. The chimpanzees were inoculated with either undiluted master seed material triply cloned or with dilutions of the same material. The undiluted master seed virus was produced from a triply cloned tube; that material was then used to expand the amount of virus by inoculating additional cells and sugsequently these inoculated cultures were harvested, providing a larger pool of virus. This material constituted the expanded master seed virus pool. This material was subsequently used to inoculate chimpanzees using either undiluted material or 10-fold dilutions of the master seed.

EXAMPLE 3

Inoculation of Animals. Chimpanzees were inoculated either intravenously or by mouth, and every subsequent week for 4–6 months were bled and checked for elevated liver enzymes (ALT, alanine amino transferase) + anti-HAV antibody. Elevations of enzymes would indicate the presence of hepatitis A illness in the animals and presence of antibody would show protection (Table 4). Clone #1 (TC passage 20 or 21) infected 11 of 15 susceptible chimpanzees inoculated intravenously or by mouth and produced a mild hepatitis in only two of these. The 11 infected chimpanzees responded with protective antibody 3–8 weeks after vaccination. Clone #2 (TC passage 20) was inoculated intravenously into 4 susceptible chimpanzees. Only 1 of the 4 animals had a very mild borderline hepatitis. All four developed protective antibody. Similarly, 1 of 2 susceptible chimpanzees inoculated intravenously with Clone #4 (TC passage 9) was infected without hepatitis but with the development of protective antibody.

TABLE 1

ATTENUATION OF HAV, STR. HM-175:ANIMAL STUDIES

| | Chimps | | | Marmosets | | |
|---|---|---|---|---|---|---|
| Passage In TC | No. | ALT Mean Max | (Range) | No. | ICD Mean Max | (Range) |
| 0 | 7 | 314 | (109–419) | 10 | 4777 | (1,631–15,980) |
| 10 | 7 | 62 | (41–75) | | N.T. | |
| 20 | 5 | 48 | (37–61) | 7 | 3516 | (1,062–10,230) |
| 20 and 21* | 10 | 60 | (38–87) | 3 | 2936 | (2,263–3,799) |
| No HAV+ | 6 | 57 | (41–81) | 4 | 610 | (483–927) |

*Triply cloned
+Noninfectious dilutions of HAV

TABLE 2

RESPONSE OF IMMUNIZED CHIMPS TO CHALLENGE WITH WILD TYPE HAV

| | Pre- | | Post Challenge* | |
|---|---|---|---|---|
| Chimp | challenge Vaccine | Challenge Anti-HAV (P/N) | Max ALT | Anti-HAV (Max):P/N |
| A-8 | TCP-10 | 9.5 | 64 | 22.8 |
| 947 | TCP-20 | 9.1 | 65 | 28.3 |
| A-53 | TCP-20 | 11.4 | 280 | 28.1 |
| A-54 | TCP-20 | 4.8 | 57 | 14.3 |
| A-55 | None | 1.3 | 402 | 26.0 |

*HM-175 Wild type $10^3$ CID

TABLE 3

ATTEMPTS TO PASS ATTENUATED HAV FROM VACCINATED CHIMPS

| Inoculum | Source | Recipient | Max. ALT | Anti-HAV |
|---|---|---|---|---|
| Acute Stool | Chimp 922 (TCP-10) | Chimp A-136 | 57 | — |
| Acute Stool Pool | Chs. 947, A-11, A-53, A-54 (TCP-20) | Chimp 992 | 46 | + |

TABLE 4

HAV, Strain HM-175, Triply Cloned Chimpanzee Response

| Chimp | Inoculum | | TCID | | Max Enz. Elv. | Max Pre-Enz. | Duration Enz Elv (wks) | 1st Ab (wks) |
|---|---|---|---|---|---|---|---|---|
| 993 | Cl#1 P-20 | $10^{-1}$ IV | | | 73 | 65 | — | — |
| A-6 | ↓ | ↓ | | | 75 | 71 | — | — |
| A-51 | ↓ | ↓ | | | 192 | 50 | 2 | — |
| A-178 | ↓ | $10^0$ IV | | | 42 | 43 | — | 5 |
| A-47 | Cl#1 P-21 | | $10^5$ | IV | 57 | 43 | — | 3 |
| A-150 | ↓ | | ↓ | ↓ | 129 | 42 | 1 | 3 |
| A-19 | ↓ | | ↓ | oral | 47 | 54 | — | — |
| A-169 | ↓ | | ↓ | ↓ | 50 | 32 | — | 8 |
| A-60 | ↓ | $10^0$ IV | | | 72 | 70 | 2 | 6 |
| A-232 | ↓ | ↓ | | | 40 | 36 | — | 6 |
| A-67 | Cl#2 P-20 | $10^{-1}$ IV | | | 78 | 68 | — | 5 |
| A-113 | ↓ | ↓ | | | 38 | 45 | — | 6 |
| A-118 | ↓ | ↓ | | | 44 | 51 | — | 4 |
| A-218 | ↓ | $10^0$ IV | | | 87 | 36 | 2 | 5 |
| A-68 | Cl#4 P-9 | $10^{-1}$ IV | | | 50 | 54 | — | 4 |
| A-52 | ↓ | ↓ | | | 55 | 51 | — | — |

We claim:

1. A method of producing a protective antibody response in higher primates by injecting said primate with a hepatitis A live attenuated virus, strain HM-175 injection which is of uniform virus composition.

2. The method of claim 1 wherein the uniform virus composition is hepatitis A virus, strain HM-175 triple cloned material of primary African green monkey kidney cell culture passage level at least 10-30.

3. The method of claim 1 wherein the live attenuated virus is triple clone strain HM-175.

4. The method of Claim 1 wherein the injection of a higher primate is a form of vaccination that confers protection against type A hepatitis caused by unmodified (wild type) hepatitis A virus.

5. A method of claim 1 wherien the live attenuated hepatitis a virus, strain HM-175 in administered by percutaneous injection.

6. A method of Claim 1 wherein the live attenuated hepatitis A virus, strain HM-175 administered by mouth.

7. An improved vaccine for mammals comprising a triple cloned hepatitis A virus, strain HM-175 that is useful after attenuation as a vaccine.

* * * * *